US009955922B2

(12) United States Patent
Shuck

(10) Patent No.: US 9,955,922 B2
(45) Date of Patent: *May 1, 2018

(54) CAPSULE DEVICE AND METHODOLOGY FOR DISCOVERY OF GUT MICROBE ROLES IN DISEASES WITH ORIGIN IN GUT

(71) Applicant: Lowell Zane Shuck, Morgantown, WV (US)

(72) Inventor: Lowell Zane Shuck, Morgantown, WV (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/597,066

(22) Filed: May 16, 2017

(65) Prior Publication Data

US 2017/0281091 A1 Oct. 5, 2017

Related U.S. Application Data

(63) Continuation-in-part of application No. 13/691,169, filed on Nov. 30, 2012, now Pat. No. 8,491,495.

(60) Provisional application No. 61/727,177, filed on Nov. 16, 2012.

(51) Int. Cl.

| | |
|---|---|
| ***A61B 5/00*** | (2006.01) |
| ***A61B 10/00*** | (2006.01) |
| ***A61M 31/00*** | (2006.01) |
| ***A61B 5/07*** | (2006.01) |

(52) U.S. Cl.

CPC ............ *A61B 5/6861* (2013.01); *A61B 5/073* (2013.01); *A61B 5/4839* (2013.01); *A61B 10/0045* (2013.01); *A61M 31/002* (2013.01); *A61B 2010/0061* (2013.01); *A61B 2562/0285* (2013.01); *A61B 2562/162* (2013.01); *A61M 2202/068* (2013.01); *A61M 2202/07* (2013.01); *A61M 2202/203* (2013.01); *A61M 2202/30* (2013.01); *A61M 2205/3303* (2013.01)

(58) Field of Classification Search

CPC ............ A61B 5/073; A61B 5/07; A61B 1/041

See application file for complete search history.

(56) References Cited

U.S. PATENT DOCUMENTS

| | | | | | |
|---|---|---|---|---|---|
| 7,918,786 | B2 * | 4/2011 | Kawano | A61B 1/00156 | 600/117 |
| 8,195,276 | B2 * | 6/2012 | Uchiyama | A61B 1/041 | 600/424 |
| 8,257,257 | B2 * | 9/2012 | Takizawa | A61B 1/00156 | 600/101 |
| 2003/0208107 | A1 * | 11/2003 | Refael | A61B 1/0005 | 600/300 |
| 2003/0213495 | A1 * | 11/2003 | Fujita | A61B 1/00059 | 128/899 |
| 2004/0204630 | A1 * | 10/2004 | Gilad | A61B 1/041 | 600/160 |
| 2005/0177069 | A1 * | 8/2005 | Takizawa | A61B 1/041 | 600/573 |
| 2005/0187433 | A1 * | 8/2005 | Horn | A61B 1/04 | 600/160 |
| 2008/0208077 | A1 * | 8/2008 | Iddan | A61B 1/041 | 600/582 |
| 2008/0294143 | A1 * | 11/2008 | Tanaka | A61B 1/041 | 604/506 |
| 2009/0088618 | A1 * | 4/2009 | Arneson | A61B 1/0011 | 600/373 |
| 2009/0143697 | A1 * | 6/2009 | Tanaka | A61B 1/00158 | 600/565 |
| 2009/0253999 | A1 * | 10/2009 | Aoki | A61B 1/00016 | 600/565 |
| 2009/0314106 | A1 * | 12/2009 | van Halsema | A61B 5/14539 | 73/864.91 |
| 2010/0331641 | A1 * | 12/2010 | Bangera | A61B 1/041 | 600/345 |
| 2010/0331827 | A1 * | 12/2010 | Shimizu | A61B 5/073 | 604/890.1 |

* cited by examiner

*Primary Examiner* — Michael C Stout

(57) ABSTRACT

This special gut microbe and chemical substance sampling technology, utilizing swallowable capsules, is for purpose of determining roles gut contents play in some 52 of most costly, in lives and dollars, of diseases with their known origin in the human gut. Gut microbes and substances are collected, analyzed, medicinal substances and objects deployed, and special provisions for attracting, capturing and preserving certain strains of microbes, and means for perturbing the gut environment and immune system are all intended to research, discover, and ultimately find both the causes and cures for the most devastating human diseases, and in the process, create gut microbiome profiles.

20 Claims, No Drawings

CAPSULE DEVICE AND METHODOLOGY FOR DISCOVERY OF GUT MICROBE ROLES IN DISEASES WITH ORIGIN IN GUT

This application is a continuation in part of application of U.S. application Ser. No. 13/691,169 filed on Nov. 30, 2012, now U.S. Pat. No. 8,491,495, which claims benefit of U.S. provisional application No. 61/727,177 filed on Nov. 16, 2012, the contents of which are incorporated by this reference herein in their entirety.

BACKGROUND OF INVENTION

Field of Invention

The present invention relates to at least one device, at least one system, at least one process and methods thereof to be used within the medical sciences, engineering, research and medical technologies, wherein the device is ingestible and untethered to perform functions of telemetry, obtaining and collecting samples, obtaining and storing information, transmitting information, perturbing an environment, sensing information and/or releasing/inserting/placing substances, devices, and/or sensors for use within or with the environment of a gut or gastrointestinal tract.

Description of the Related Art

Medicine has advanced in all major human body systems, such as cardiovascular, neurological, muscular and skeletal, but the intestinal tract still remains much of a mystery. Though there are instruments and devices which can be used for endoscopy/colonoscopy, there are sections of intestines that remain unexplored and are found incredibly difficult to collect and preserve samples there from. Even these upper and lower extremities, which can be viewed by camera and can only be treated for visible damage, such as polyps or ulcers. The roles bacteria play in the intestinal tract are generally not understood, except that there are "good" and "bad" bacteria. In fact, only a few of the estimated thousands of strains of bacteria are known, or have been identified, much less characterized and their roles determined. One known device is of a camera pill that can now be swallowed and pictures taken throughout the intestinal tract, but visible inspection does not address the scientific mysteries of diseases and their causes or cures.

In order to understand the causes of diseases and illnesses believed to be originating somewhere within the entire human intestinal tract, basic science and engineering data are necessary to analyze the biochemical, biological/physiological, and bioengineering processes taking place therein, along with the flora of microbes and the roles they play in the digestive and other involved processes. Currently, in most gut-related diseases, only the symptoms are being treated under a wide variety of named diseases, Celiac being an example, while the causes remain unknown. In order to advance the medical science, bioengineering and technology to the same levels of DNA, microbiology in general, etc., as in other anatomical systems, sufficient in-vivo data must be available to develop intrinsic models and identify physiological and biochemical processes, as opposed to superficial and grossly inferior statistical inference methods.

Specifically, what is not known within the human gut is a huge void in medical science and an aim of this invention, such as: the biochemical products existing for any specific diet are not known as a function of the gut length x; the biochemical reactions taking place along the gut are not known as a function of the gut length x; the microbes existing at any point within the gut anatomical system are generally unknown and unidentified; the byproducts of all microbes their toxins, exotoxins and endotoxins, and virulence factors and enzymes existing within the gut are likewise unknown, much less as a function of x; the aerobic/anaerobic distribution and associated conditions are vaguely known, but not as a function of x; the interaction of a) the normal biochemical reactions, b) the microbes, and c) the microbe byproducts are totally unknown, and believed to be a major source of several major diseases; the data necessary to identify and characterize physiological, biochemical or other bio-engineering processes, or construct any sort of a scientific, mathematical or engineering model of any component of the gastrointestinal system ranging from the stomach, duodenum, jejunum and ileum, through the colon are totally unavailable for healthy individuals as a function of x, much less for unhealthy individuals. Some 15 categories of bacteria have been broadly identified within the Phylogenic Tree as existing within major components of the gastrointestinal tract. The microbial flora distribution for the gastrointestinal tract has been broadly cataloged for major components of the system, and some general aerobe and anaerobe distributions and populations are broadly known for major components in healthy people, but not as a function of x, much less for people with diseases. More importantly, what about those new or previously undiscovered, or unidentified and uncharacterized strains that may be contributing to diseases. Thus, in general, bacteria strains and colonies and their populations, population densities, habitats, and characteristics and contributions to the digestive process are only very vaguely known in healthy individuals, and largely unknown in unhealthy individuals, much less as a function of x. 9. The characteristics of some bacteroides, individually, or in serial, or parallel, in conjunction with others and their independent diets and byproducts in conjunction with the human digestive processes are generally unknown, much less as a function of x; and/or additional critical information needed includes the ratios of solids, liquids, and gases, as well as, their compositions, temperature, partial pressures, and other variables. These quantities and variables are totally unknown in the intestinal tract, for any specific diet, especially for unhealthy individuals, much less as a function of x.

There are many reasons why the human gut is largely unexplored, except for post mortem autopsies, which do not reflect much of the most important living dynamic phenomena and conditions. Meanwhile, medical treatments for symptoms of major diseases and illnesses, based upon hypothetical or worse, biased statistical data, form the basis of thousands of medications, and unnecessarily occupy valuable time of many medical professionals and clinics at a great cost to our economics, which could otherwise be focused on permanent cures based upon causes instead of symptoms, and based upon intrinsic models of fundamental biochemical processes.

The inaccessible regions of the most important anatomy of the gut, and the lack of technology to explore, discover, and experiment in an in vivo manner, and then administer medications and measure in vivo the immediate results, has constrained and obstructed beyond description throughout history the advance of medical science pertaining to the gut. A competent research effort investigating any animate or inanimate system should attempt to identify the fundamental multidisciplinary scientific principles of science and engineering upon which the system is based and functions, and then develop quantitative measures of those principles. The inaccessibility of the gut, and heretofore lack of technology, has resulted in speculation and statistical correlation of symptoms from a distance throughout history as a means of researching the gut. The need for in vivo technology became immediately apparent. Eventually the various concepts were condensed into three basic tools, Capsules A, B and C, and additional supporting technology and infrastructure, that when ultimately developed and implemented as a system, should address the immediate need to serve a creditable scientific and engineering systems approach to introduce gut in vivo technology.

The applicant has advanced the state of the art technology for discovery of microbes and their byproducts that contribute to the normal and abnormal human, or other animal, digestive processes and the consequential processes introduced by autoimmune system responses. In summary, these contributions are herein referenced in U.S. Pat. Nos. 8,491,495, 8,915,863, 8,926,526 and 9,215,997. These referenced patents serve the purposes, respectively, of: '495) in Capsule A, profiling the entire GI tract microbes in each patient simultaneously at each point in space and time within the gut upon external command along with the chemical substances created as byproducts from the existing populations of microbes at said points in space and time, including the constituent normal food products as at some points referred to as chyme, which include secreted acid and enzymes; '863) in Capsule B, conducting all phases of research on all aspects of the normal and abnormal digestive process, and processes that lead to or constitute diseases of which some 53 major human diseases have been referenced as having their origin in the gut; '526) in Capsule C, a patient diagnostic and treatment capsule, wherein sampling of all sorts and perturbing of the gut is performed to diagnose patient conditions, and wherein substances can be deployed to treat specific ascertained conditions, and post treatment results can be measured, are specifically claimed; and '997) incorporates the various methodologies, processes, protocols and broad techniques employed to render a new human healthcare system when all 4 patented technologies are utilized appropriately in patient diagnostics, treatment and research applications. Substances are all-inclusive of any gaseous, liquid, solid or gel state, and of any physical, chemical, or other nature. Deployment of substances may include small objects of micro shape and size to perturb the autoimmune system, including all possible combinations, such as, "seeds" for prostate cancer treatment, which at the molecular and cellular levels may induce responses from the autoimmune system it may recognize as a threat.

This invention is intended to provide this and more enabling science and engineering data and information that can lead to revolutionary improvements in general health care. This invention is intended to provide a device, process and method thereof to be used for at least one of collection of samples, obtaining information, or releasing materials or objects for diagnostic and research purposes within the medical and science fields pertaining to the path of the gastrointestinal tract and surrounding paths of travel. Embedded in all of this is to isolate, condense, shrink, and constrain the research defined "system" in order to reduce the huge number of variables in any animate system to a tractable number, using extreme precision and resolution along with extreme protocols. Gut variables number over 6,000 due to the 3,000 plus bacteria strains and 3,000 minimum byproducts as their populations vary from 107 cells/gram in small intestine to 1011 in colon. This new technology is designed to: a) compress longitudinal studies/research from 20 years or more to weeks or months in some cases, and in other cases from months to hours, days or weeks. b) reduce the numbers of variables by 3 or 4 orders of magnitude (104), c) increase sampling precision and resolution by 4 or 5 orders of magnitude (105), d) expedite test cycles to 2/week compared to months to enhance repeatability, expedite discovery, reduce extraneous variables, and e) allow quick trial and immediate evaluation of critically important variables, such as diet and medication effects, among several other improvements compared to current methodologies.

SUMMARY OF THE INVENTION

At least one embodiment described herein are designed as a means of discovering, characterizing, and treating the causes of the major 53 human diseases with known sources being in the human gut, and believed to be effects occurring at the heretofore inaccessible locations in the gut at the molecular and cellular levels. Thus, this technology and the associated methodologies form an entirely new human healthcare system based in the GI tract, through which substantive research can be conducted, and diseased patients diagnosed and treated. This is absolutely necessary because of the conditions created as a result of microbial functions that result in various immune system and other organ responses, and bioengineering-biomechanical-biochemical engineering phenomena, that contribute to any and all of these 53 diseases with some 34 combinations of symptoms, that can show up in any organ or in any neurological, cardiovascular, muscular, or other system after stealthy existence in the gut for many years, and revealing only elusive symptoms that can only be treated.

The disclosures described below, are of such nature to constitute an entirely new human healthcare system, and to revolutionize and create an entirely new hybrid, multidisciplinary, field of gastroenterology and establish entirely new university graduate school multidisciplinary curricula syllabi, and new hybrid multidisciplinary university research programs, along with new government medical research programs and facilities. Further it is seen possible to establish a new medical industry business structure and plan which can create technologies within gastroenterology and robotic medicine based in the GI Tract that has promise of discovering the actual causes of many of the top 53 human diseases, of which not one cause is currently known. This list includes the number one human health disease killer: heart disease with a known origin in the gut.

The simultaneous sampling and analysis of even just microbes and their substances has not been properly done within the gut. To simultaneously sample/analyze and associate damaged tissue, microbes, and chemical byproduct substances at the cellular and molecular micro scales is the ultimate theoretically possible capability for research and solution of the mysteries of disease causes throughout the entire history of the medical profession and medical science and is one resulting advantage of the invention.

The embodiments herein comprise the means to function as, and serve various purposes, such as: 1) in vivo instrumentation systems, 2) data acquisition systems, 3) data transmission systems, 4) process control systems, 5) onboard lab-on-a-chip sensor/transducer systems, 6) monitoring systems, and 7) base of operations and launch platforms for various mini, micro, or nanobots operations involving either sampling, perturbing, or treating the various components of the gut environment in various combinations and sequences. The device and methods further comprise the means to perform extracting and preserving samples in the same geometry, order, state, and composition in which it naturally existed within the gut environment for the purpose of exploring, defining, and characterizing each of the following, and determining associations and correlations with each of the following as a method to determine the actual causative effects and the actual causes of various diseases at the molecular and cellular levels involving: a) microbes b) chemical and biochemical substances, c) mucosal tissue, and d) sub-mucosal tissues, and furthermore, as may be obtained from i) needle biopsy columnar form and structure, ii) swab or smear type sample structure, and iii) slice of layered naturally occurring substances, wherein said isolated and preserved samples may be of various spherical, cylindrical, or rectangular shapes and the pertinent dimensions may be of the order of 0.15 inches or less; wherein the relationships among a), b), c) and d) are mapped and plotted using 3-D graphics along the GI tract as a means of characterizing the nature of and causative mechanisms of various diseases. The device and methods further comprise wherein substances may be administered from the middle of the device and various information, such as, pH, temperature, noise, microbial activity, molecular and cellular based variables, and the like are determined, sensed, and/or monitored upstream and downstream as functions of time and gut space locations. The device and methods further comprise wherein the nanobots may be a) fixed or mounted only within said capsules, or b) tethered from capsules, c) autonomous and retrieved to base, or d) autonomous and allowed to drift in the normal course of matter moving through the GI tract. The device and methods further comprise wherein the perturbing performed includes addition of any form or constituency of a) energy, or b) matter of any electrical, chemical, mechanical, acoustic, or thermal type, for example, and targeted at any tissues or substances including and ranging from the macro to the cellular, molecular and ionic levels. The device and methods further comprise wherein pertinent variables are measured to ascertain microbial species and strain populations spatial and event associations with all gut variables, parameters, and conditions as may be established by either normal or controlled diets or administered drugs or other perturbations. The device and methods further comprise means to generate comprehensive analysis, construct mathematical, physical, bio-chemical, biomechanical, and the like models to simulate the conditions to facilitate not only post-disease cures, but also future preventative measures to educate and inform the general public, as well as, the medical profession.

The embodiments include a comprehensive process, methodology, mechanical devices, protocols, and computer-based data acquisition, reduction, analysis, display, and modeling hardware and software system for gathering and/or extracting in-vivo biological specimens from beginning to end of the human gut and digestive system. Features and functions include preserving the sample's in-vivo environmental integrity, conducting sample chemical analyses, microbe strains/colonies identification and characterization along the entire intestinal tract, compiling and analyzing the data, displaying it in real time retroactively using known computer graphics simulations as it was obtained, which will allow construction of mathematical, physiological, biochemical, and other engineering models, and delineation of causes of diseases originating within the gut. This system will also provide data for attending physicians to assess and classify damages and diseases, and prescribe diets or medications. Additionally, provide physicians, when a second patient testing and evaluation is conducted, with fast quantitative results as to the effectiveness of prescribed diets and medications quicker, as opposed to waiting for months to see if treatments are working in any visible or statistically significant, or other largely qualitative evaluation manner. The entire process will eliminate much of the inferior statistical methods of testing large populations over extended periods of years to correlate symptoms and cause/effect relationships of diseases are indeterminate from such tests because of the 6,000 unknown variables that create coincidence statistically. In contrast, this invention can result in development of intrinsic models based upon basic principles of science and engineering at the molecular and microbe, as well as, macro levels. As a result, the various fields in the micro world, such as microbiology, nanotechnology and nanoengineering, can be merged with those scientific and engineering fields in the macro world to integrate and create more holistic understandings of the involved processes within the all-important human gut, and then appropriate cures for many major diseases should occur.

Another embodiment of the invention includes a device ("Capsule") specifically designed for physicians to use to treat patients, and also in the process, generate massive data profiles of patient illnesses and diseases with all of the patient-specific data history that can be helpful in advancing medical science and understanding of the gut system, and its important roles in other human organ diseases. This device and method also uses a belt-pocket cartridge system to deliver substances or objects to the gut in specially designed pockets and compartments for use either as part of diagnostic or treatment processes, or functions to be performed as the Capsule passes through the gut, or to deliver substances or devices, such as medicines, chemicals, bacteria, or nanomachines in a safe and efficient manner to specific points, and based upon criteria as may be established to be sensed in vivo and interactively deployed, or as may be deployed by telemeter methods. This device is a critical step in a continuing research project to develop a comprehensive gut health care system. In particular, this Capsule can be allowed or commanded to, while in a particular region of the gut corresponding to specific anatomy or various criteria, release substances or devices as prescribed by a physician of adequate quantity and protected from upper gut enzyme and acidic environments, thus of controlled composition and purity to be consumed, or interacted with microbes or other existing conditions within said specific region. Upon release, and simultaneously, or immediately after any prescribed time "t.sub.1" following said medication or process delivery, begin to sample the associated microbes and chemical substances at prescribed time intervals t.sub.2, t.sub.3, etc. and preserve them for later in vitro analysis as feedback to physicians, to determine if the medications were successful as intended. In some cases, in vivo monitoring may provide proof of success of procedure, or indicate a needed iteration in procedure, of which in some cases, may be feasible. The Capsule features include, for example, the delivery not only of medications, but new safe substances that may be effective in dissolving the viscoplastic encapsulating gel or plaque like material or other adverse microbe habitat created substances, that totally corrupts villi functions and leads to their disintegration, as evidenced in autopsied Celiac patients. Features comprised within the Capsule enhance the success of application of this instrument to a wide range of gut conditions, and to achieve overall success of each of a multiplicity of purposes and candidate missions. The cartridges in particular are designed from materials appropriate for specific medicinal substances, quantities, sequences, and monitoring means, and adapted conventional physician and pharmaceutical methodologies and protocols.

Another embodiment of the invention is based upon a continued rationale for first gaining access to all parts of the GI tract, sampling, testing and analyzing all aspects of the biological system, utilizing in the most productive manner the data mined, discover disease causing processes and interrupt them, and ultimately characterize and create holistic models of the gut system. Access and information mining is accomplished in 3 steps of which this invented device provides. The cartridge system simultaneously collects samples of microbes and substances within the human or other animal gut, and preserves them for later in vitro analysis, but in addition, to also delivers substances or objects to the gut in specially designed pockets and compartments for either use as part of the process or functions to be performed as the Capsule passes through the gut, or to be accessible to microbes for processing. In particular, the Capsule can be allowed or commanded to, while in a particular region of the gut corresponding to specific anatomy, release substances protected from upper gut enzyme and acidic environments, thus of controlled composition, to be consumed or interacted with microbes within said region, and immediately and simultaneously sample the associated microbes and chemical substances and preserve them for later in vitro analysis. Release or exposure of the substances to microbes can be controlled over predesigned desirable times and distances repetitively within the gut, and samples can be collected in immediate capsule vicinity, upstream and downstream, to provide fine resolution of the results of such substance interaction with microbes, in particular of such microbe strains as may have a special affinity for particular substances, or as may create certain measurable conditions or processes of interest. The invention provides for the purpose of discovering the specific microbes and their biochemical created substances, such as toxins, exotoxins and endotoxins associated with specific diseases, and the specific processes through which the autoimmune system and other anatomical components of the gut, such as the villi in the small intestine, are interrupted and corrupted from performing their intended functions, which directly leads to increasing stages of various illnesses and diseases. The ultimate result is intended to create explanations, understandings and conclusions pertaining to gut functions and gut based illnesses and diseases, based upon basic science and engineering principles and processes, instead of statistical correlation of extra body symptoms variables where probabilities of discovery are less than one in millions.

A comprehensive system for gut in vivo exploration, discovery, characterization, research, diagnostics, and treatment comprising three different ingestible apparatuses and their associated methodologies, is invented and under development to provide researchers and medical professionals the tools needed to discover the causes of gut-based illnesses and diseases, treat, and hopefully cure them. The three apparatuses are capsules, each specifically designed to perform fundamental functions when ingested under the care of a patient's physician, or other medical profession orders. As an in vivo health care system, the gut processes of digestion can be analyzed on a very small incremental step by step process from the mouth to the anus as a function of the length of the gut "x" and at any point in time "t", including simultaneous chemical substance sampling and testing, along with the associated microbes. The system accommodates testing of diets and the results in an "as is" condition, or as may be modified by substances delivered to any point x within the GI tract at any time t, and the upstream and downstream results simultaneously measured. This capability greatly broadens the horizon for dietary studies with elimination of thousands of extraneous variables. Likewise, medications, or autoimmune response test substances, antibiotics, or other substances for whatever reason, can be delivered in a prescribed manner to the point of interest and the consequences or results in an interactive mode, immediately and simultaneously sampled and monitored at the delivery point and time.

When used as a System, innumerable subjects and issues of a complex matrix nature can be investigated and treated, which will quickly result in the creation of in vivo gut Big Data, of which little currently exists. Many capabilities of characterizing, analyzing, diagnosing, and treating diseases of the gut are enabled when systems logic and rationale are employed in forming a new perspective of the gut, in context with this System associated new technology capabilities and applications. Of course, diagnosing and treating diseases is the ultimate objective, but not to be undervalued as part of the process leading up to such results, is the quantification and characterization of the basic science and engineering principles involved or prevalent in the primary functions of the gut as a system. The gut is one of the most complex systems that can be imagined, involving coupled, time-dependent processes and variables both at the micro and macro levels and of many disciplines. Utilizing distribution functions of hundreds of variables allows the gut to be raised to levels of abstraction, wherein an entirely new class of methodologies and evolutionary technologies can be considered for any aspects of gut analysis, diagnosis and treatment. Such abstraction/quantitative capabilities can include creation of simulation models for a variety of purposes. The individual capabilities of each Capsule A, B, or C should raise the scientific knowledge level and the medical diagnostic and treatment levels of the gut by orders of magnitude, and with the combined capabilities as a System, another order of magnitude or so. This in vivo System delivers these capabilities, and therefore, should greatly expand the horizon for gut health care, and enable many new technologies, institutions, medical professionals, businesses, and industries for gut applications and opportunities.

The present invention solves the problems discussed above by providing an in vivo gut technology system including new investigative and health care methods and processes, and composed of three individual, stand-alone inventions, that when combined logistically, strategically, and applied in combinations, comprise a synergistic, multidisciplinary system with diversified applications, diagnostic and research methodologies for gut healthcare and total body holistic macro healthcare through facilitating discovery of causes of diseases and subsequently their cures.

Each of the 3 independent invention Capsules A, B, and C, which make up part of the in vivo gut technology system, can create independent Distribution Functions (DFs or DF) of hundreds of variables as functions of gut length "x" and other variables, and each set of DFA, DFB, and DFC. innate to, and limited to the innate capabilities of, their respective capsules create synergistic system capabilities.

The system and enabled DF and other quantitative capabilities in various combinations can comprise new research methods and processes of gut investigation, and new research tools.

The system-enabled DF and other quantitative capabilities in various combinations can comprise new gut diagnostic methods, processes, and tools for clinical applications by physicians of many medical professional disciplines.

The system-enabled DF and other quantitative capabilities in various combinations can comprise new gut treatment methods, processes, and tools for clinical applications by physicians of many medical professional disciplines with specific patient gut illnesses identified, treated, and results measured at the point of event, and incorporated into a DF and abstract numerical or graphical model where comprehensive reference can be made for any reoccurrence.

The system of the present invention provides capabilities, samples, data, and data reduction and analysis is such manner to actually provide for discovery and disclosure of the causes of gut-based illnesses and diseases, as compared to existing inferior technology capabilities of largely extra body researching, correlating and treating the symptoms.

The system of the present invention can reduce the number of variables normally exceeding, perhaps 10,000 variables, by orders of magnitudes for researchers or clinical physicians, with extraneous variables eliminated and only patient specific variables remaining for comparison by utilizing combinations of Capsules A, B, and C along with results from personal physician prescribed applications, such as, specific point testing, sampling, and data interpretation.

A new In Vivo Gut Technology System (System) comprising new investigative and health care methods and processes, and composed of three individual, stand-alone inventions, that when combined logistically, strategically, and applied in combinations, comprise a synergistic, multidisciplinary system with diversified applications, wherein said capabilities in various combinations comprise new gut Abstraction Methods, Processes, and tools for quantitatively and mathematically representing gut functionality and dysfunction, general behavior, characteristics, healthy and unhealthy, and miscellaneous features in a manner suitable for computer software and hardware applications.

The hardware and software applications can include, but are not limited to, numerical simulation models for numerous applications, passive and interactive diagnostic models and systems, passive and interactive treatment models and systems, and interactive database construction, as well as, model construction for specific illnesses and diseases.

The hardware and software applications can further include, but are not limited to, Applications (APS) for generalized guidance in introduction and development of the new in vivo gut technology System.

The hardware and software applications can include, but are not limited to Applications (APS) for Business Development, Business Management, Warehouse development, Prescription Creation and Management, and Technology Transfer, and incorporating all aspects of hardware and software applications for this new in vivo gut technology introduction and development as may be accommodated by abstraction of gut phenomena associated with said System. The System can generate not only qualitative or circumstantial, but quantitative proof or disproof of hypotheses for digestion processes, gut functions, dysfunctions and disorders, and causes of illnesses, diseases, and microbe based phenomena. For example, the system can be used to prove or disprove important hypotheses pertaining to effects of various microbes processing gut substances in a cascade manner that may create toxins, exotoxins and endotoxins, and autoimmune responses, which can result in discovering the cause of certain gut diseases.

With all combined data from System applications and as a result of System existence, such as all DFA, DFn, and DFc in conjunction with all patient physician and research generated volumes of data over a period of time, sufficient knowledge and data can be generated and accumulated for construction of holistic, quantitative models of the human gut.

A new in vivo gut technology System, comprising new investigative and health care methods and processes, and composed of three individual, stand-alone inventions, that when combined logistically, strategically, and applied in combinations, comprise a synergistic, multidisciplinary System with diversified applications, wherein said capabilities in various combinations comprise an Enabling System foundation and framework process, upon which new gut-based institutions, businesses, and industries can be created.

The System enabling capability results, of necessity, in new higher education multi- and interdisciplinary professional training schools or colleges with specific interdisciplinary curricula designed for this new gut in vivo technology System.

As an enabling technology, the System based higher education institutions offer multi- and interdisciplinary educational degree programs based upon matrix organizational structure for efficiency and effectiveness in communications, multi and interdisciplinary teamwork model development, sharing of equipment and facilities, System reflective course syllabi, and overall results-oriented performance objectives and goals, all in contrast to traditional, obsolete, walls and halls of compartments and departments of isolation organization charts.

The System based institutions are created and so structured for research purposes. The System's new enabling framework embellishes, incorporates, provides for and facilitates application of, and participates in, complementary bio-nanotechnology and nanotechnology, especially sensor development, and the creation of new related spinoff Gut In Vivo System Technologies.

A new Gut Laboratory (GL) enterprise facility and business with potential spinoff technology development is specially designed and created to accept, handle and manipulate System collected samples of chemical substances with accompanying microbes, and preserve them until such time said samples are tested and data collected for said intended System purposes, and said samples are appropriately disposed, and wherein said Laboratory is comprised of new specialized, modified, and adapted instrumentation, such as SEMs, spectrometers, chromatographs, and substantial computer-based detection, testing, pattern recognition, and other instrumentation, as well as, voluminous data processing and analysis.

System combinations of belts, pockets, chambers, cartridges, sensors, and provoking or perturbation substances, medications suitably packaged, strategies and methodologies as herein disclosed all together in their entirety, constitute an "n-dimensional" matrix of in vivo gut education, research, diagnostic, and treatment medical healthcare system, upon which entirely new type of warehouse, special substance preparations, special laboratory testing facilities, physician education and specialized training and expertise development, substance prescriptions, distribution, and pharmaceutical-like medical orchestration system, constitute an entirely new multi-disciplinary medical education, gut research methodology, healthcare delivery methodology and system, and new Gut Technology Industries (GTI's), each to be implemented as a part of a comprehensive new gut healthcare delivery system.

The exemplary embodiment is understood to provide a capsule device and method thereof capable of obtaining and preserving samples of substances from the surrounding environment where it may be used; further capable of releasing or activating substances or devices stored within the device into the surrounding environment; controlling the device to move and navigate within the surrounding environment; and controlling the device to perform functions or actions controlled by a controller housed within the device, which may be triggered remotely or internally.

DETAILED DESCRIPTION OF INVENTION

General Embodiment

A comprehensive Research and Diagnostic System is invented and designed that consists of the necessary component parts to acquire, store, and preserve intestinal samples in in-vivo conditions, including during such time as comprehensive testing, analysis and characterization of the matter consisting of both inanimate substances and microbes, as existed in-vivo at the exact same location and time, as a function of the length of the entire intestinal tract, is performed. The methods, processes, apparatuses, research procedures, and patient application protocols are all part of said invention, which constitutes an entirely new technology for patient diagnostics, and advancement of scientific and engineering knowledge of the human gut.

The Research and Diagnostic System (RDS) consists of a Pill or Capsule that can be swallowed along with any typical, patient preferred diet, or a research designed and prescribed diet, and/or a prescribed total protocol. The Capsule acquires samples of matter continuously along the entire intestinal tract and stores and preserves it in "in-vivo" conditions until it can be inserted into the Incubator and Manipulator, and subsequently the Analyzer. The Capsule can also deliver said samples to any other laboratory instruments capable of testing said samples for any known variable or reason, or even frozen and used in future to-be-determined tests.

The Incubator and Manipulator functions to preserve the environment in which samples were obtained and transfer said samples into other storage or testing apparatuses.

The Analyzer is a work station of multiple testing equipment and apparatuses that have been specifically designed, or selected and modified, with specific probes designed to interface with the samples containment vessel, (as exemplified only as an example, the thin film encapsulated belt of samples) and perform a large variety of chemical, physical, microbial, materials, and other tests to determine their compositions, basis and origins of formation, genetic makeup, and numerous other characterizations. The Analyzer consists of chemical and physical probes and a variety of spectrometers and microscope devices, chemostats, that in combination can perform chemical and biological tests to identify chemical compositions and characteristics of the matter, and identify and characterize microbes, their population densities, aerobes and anaerobes, all of which exist and are sampled simultaneously along the entire intestinal tract as a function of length x. It should be noted that, depending upon the specific purpose of investigation and use of the RDS or specific protocol, not every sample will need to be tested by all of the equipment and apparatuses contained at the Analyzer work station, as a means of reducing total cost and time for obtaining the specifically desired information.

The final component of the RDS is a laboratory Computer-Based Data Acquisition, Reduction, Analysis, and Display System (CBDARADS). This system consists of conventional computer-based hardware and software modified and programmed to acquire all raw data from the Analyzer, or other sources of data and information resulting from tests on the subject samples, or other scientific data available from any source, and process said data involving all phases of data reduction, conversion, analysis, interpretation, and automatically displaying it in various forms of computer, and computer animated graphics, including 3-D, or N-D as many variable combinations other than x or t may be chosen for animation. Many software subroutines are written to make calculations utilizing said data, and presenting it in meaningful formats to specialists for easy and fast interpretation.

It is important to note that at this point of discussion, and for simplicity and clarity of describing this invention, the Capsule has been described briefly above as a passive sample gathering apparatus, wherein all testing of the samples collected as a functions of x and/or t are performed, and data are stored in bench-top elaborate, sophisticated laboratory instruments of substantial size and space requirements. This distinction is made for a host of reasons. First and foremost is because the system described to this point can be fabricated and implemented immediately without futuristic, miniaturized, instrumentation development. The Capsule described up to this point will now be delineated as Capsule A, because it is a passive sample intake form of sample collector, wherein no electronics, measurements, tests, instrumentation, or data acquisition are made or contained therein.

In contrast, there is also Capsule B included as part of this invention, where internal and external capsule measurements are made by sensors and transducers mounted on the surface, as well as internally, within the capsule to make real time measurements, store the data, and simultaneously transmit it externally from the human body in real time. At the present state of technology development, this Capsule B as herein defined is extremely limited in capability. However, part of the objectives of this invention is to initiate or trigger a suitable in vivo miniaturized instrumentation and data acquisition/transmission development revolution for better and immediate patient internal diagnoses and rapid development of in-the-gut technology. Measurements presently included in Capsule B are temperature-differences referenced to body temperature in the mouth, pressure differences/fluctuations along with pulse, pH, perhaps O.sub.2, and hopefully, other gas component compounds of hydrogen and sulfur. Capsule B, with on-board electronics, is also capable of releasing or injecting stored substances, ranging from medications at some given instant, or dyes, for example. In this regard, this invention disclosure is also a call for others of all disciplines for R & D of in vivo capsule compatible sensors and transducers. Likewise, this patent disclosure author also anticipates filing new separate invention disclosures for such instrumentation. It should be noted that this invention also includes the method and process of integrating Capsule A and Capsule B functions into one capsule as the technology is advanced.

RDS Components, Methods, and Applications Detailed Descriptions

1. Capsule A

The Capsule performs a number of distinct functions. First, it collects simultaneously partially digested biochemical products and microbes (including all Bacteria, Archaea, and Eukarya as in the Phylogenetic Tree which includes viruses and fungi) existing simultaneously at every desired point along the intestinal tract. Second, it encapsulates said samples and preserves them in a sealed environment ready for transfer, using the Incubator and Manipulator, to the Analyzer for examination and testing by the probes in it, or by other instruments in any other laboratory. The samples are taken at any pre-determined, programmable rate or frequency, and the time is recorded as the Capsule passes through the intestinal tract, which may be typically from a couple to 30 hours. The progress and exact position of the Capsule can be monitored and tracked, as a function also of time, by various remote sensing methods such as x-ray or MRI, or active telemetry from the Capsule accompanied by a receiver worn on a belt. As one particular design of Capsule A, called, Capsule A.sub.1, for now, samples are collected and stored by a wafer battery-powered motor driven thin, sterile, ribbon-belt of pre-designed length, which contains indent pockets of various prescribed volumes, and shapes spaced in pre-designed patterns to accommodate sampling frequency and total number of samples quantity. As each sample is obtained, a sealant layer of sterile film is pressed against the belt to encapsulate the sample and separate it from matter downstream, and preserve the entire environment under which it was obtained. The motor speed can be set according to the appropriate designed protocol prior to ingestion. The sample collection compartment shapes and sizes are pre-designed to accommodate a variety of microscopic methods and instruments, and designed test objectives and methods, so the samples are ready for both microbiological and chemical analysis. Each light wave opaque shell or housing of the Capsule, and internal cartridges, and sample belts and tubes also have unique serial numbers. The ends of the capsule are attached by fine machined threads and sealed with miniature O-rings in such manner for ease of assembly of motor, battery, and sample film indexed belts, spools, drums, and drive-train cartridge. Among the many variations to accommodate specific experiments and purposes, the curvature of the ends of the Capsule is also of prescribed algebraic equations with three basic designs: a) to accelerate with minimum energy passage of Capsule through the intestinal tract and thrust it against intestinal wall, b) to accommodate sampling on a radial basis across the circular/elliptical cross section of the intestine, as opposed to the normal longitudinal sampling up against the wall of the intestine, and c) to provide a maximum energy or drag of flow through the intestine matter, such that the Capsule only progresses with the normal progression of the digested products. The lengths, diameters, and shapes of the Capsules are also designed within the various intestine system constraints, such as intestine folds and the sphincter muscle. The spooling-indexing means incorporates multiple drive, tensioned take-up and idler spools mounted in a cartridge with forward/reverse spooling capability. The cartridge also includes the spools of sample hermetically sealing thin film that is permanently attached to the sample collection belt as it is deployed and samples collected. A fine mesh grille attached to the capsule housing separates and prevents the sample collecting belt from touching the lining, epithelium, villi, or obtrusive parts of the intestines. The two spools for sample film storage can also be removed from the capsule sample acquiring cartridge and placed robotically or manually into another storage capsule, or a Reader-Analyzer cartridge with a similar indexing drive motor that allows for variable spacing between dispensing and take-up spools, and x-y traverse by micro indexing table for sample automated testing or placing on various microscopic examination attachments. In this manner each indexed sample pocket can be individually tested, manually or automated, using various wavelength spectrographic or SEM, or numerous other microscopic means, including, for example, pattern recognition and microbe behavior hardware/software technology.

2. Capsule B

There is no allusion that many essential tests and analyses as described below in the Analyzer and CBDARADS can ever be adequately incorporated within an in vivo ingested capsule. However, Capsule B not only incorporates currently feasible technology, but becomes a goal and symbol for new in vivo capsule-based technology development. It is that vision of improving diagnostic and scientific and engineering technology for improving human health that is embodied within the generic Capsules A and B, and their hybrids (AB) and having the world scientific community contribute thereto.

Perhaps the ultimate greatest current benefit may be a result of on-board electronics, which creates five basic options: a) actively on demand, or passively collect samples, b) make measurements, process the data, and either store it or transmit it in real time, or c) make calculations from the measurements and take action based upon the calculated results, or d) make injections or releases based upon preprogrammed time or location parameters, or most importantly, e) take measurements, either of the chyme or other lower intestinal tract substances, or microbes, or from the human body responses, such as pulse rate or an autoimmune response, make calculations on those data, make decisions based upon those data, and execute preprogrammed commands based upon values of said processed data. This interactive capability of Capsule B is huge, because it provides among many options, to apply medication or any chemical for any purpose at an exact location at an exact time, based upon for example, an immediate feedback response from the human body, or other conditions existing within the intestinal tract.

3. Capsules A and B as Multiple Evolutionary Components

The capabilities of the sampling and in vivo measuring capsules, A and B, and their hybrids AB, of necessity must conform to the demands and characteristics of the system being researched and investigated for whatever purpose. It is important at this point to digress momentarily to discuss the nature of this system to be investigated in order to give meaning and purpose to the various designs of capsules A, B, and AB.

The Human Intestinal Tract to be Investigated

The entire human food ingestion-digestion tract may be regarded as having such major components as the mouth, esophagus, stomach, small intestine and large intestine, each having major distinct roles. The conditions within each vary widely from a food processing or an instrumentation perspective. There are also smaller scale functioning components within each of these, which need monitoring and modeling, as well as, the progressive changes to the food products as it passes through each major component. For simplicity at this point, consider the cross section at any point along the total ingestion-intestinal tract as a function of the length x, where x=0 at mouth, and x=L at anus/rectum, and at each cross section the shape is a function of radius R and angle theta. Just consider the gut for simplicity now, as having an elliptical or circular tubular cross section through which liquids, solids and gases pass as a biochemical reacting slurry in varying ratios. The cross sectional velocity, as in any tubular fluid flow, has some form of a parabolic profile, wherein the velocity is maximum at the center and zero at the outer boundary wall, i.e. V.sub.R=0 at center of gut is max, and V.sub.R=RW at the outer wall is zero. Also, at the vicinity of the outer wall there is a boundary layer across which the velocity normally goes to zero in a closed impermeable tube. However, in the human gut, mass and energy pass through the permeable wall eventually into the bloodstream via villi, and other means in the colon, where liquids are extracted. This “boundary layer” according to this author’s discovery plays a major role in the digestion system, nutrient filtration and mass transport processes, and even more importantly, the sources of causes of major diseases.

Therefore, any sampling capsule must accommodate these conditions and all phenomena to be investigated therein, ranging from the processes, the sampling substances and their phases, to the microbes therein as functions of radius, angle theta, and x. For this reason, the capsules A are really A.sub.i,j where i=1 to m, to reflect different capsule designs, and j=1 to n, to reflect the diseases or phenomena to be specifically investigated. The j=1 category is for general purpose, comprehensive sampling for any/all purposes ranging from research, to patient testing, and education. For purposes of illustration, Capsule A.sub.1,1 had a specific, unique design to sample within the boundary layer adjacent to the outer wall of the intestinal tract. Now, Capsule A.sub.2,1 is of another distinct design to sample for general purposes, but from the center of the intestinal tract, wherein instead of a thin belt collecting samples from the outer peripheral slit in the capsule housing, the sampling intake is through a port of selectable diameter D in the center of the capsule. Also, in this unique design, substances and microbes simultaneously are pulled into the port by a helical auger type of central construction that gives positive displacement at a prescribed design rate, to not only force sampling, but can also give a self-propulsive characteristic to the capsule for the excess substances passed through and not retained as samples, wherein the design ratio of sample volume/extruded through volume can go from a small fraction, e.g. 0.1 where propulsion force is maximum, to 1.0 wherein all intake sample is saved and the propulsive force equals zero. The samples are stored within Capsule A.sub.2,1 to preserve their identity and integrity, either on a similar belt with pockets and a sealing cover as in A.sub.1,1, or in single or multiple impermeable storage tubes or chambers as a result of the auger forcing the samples through in a positive displacement method, depending upon the specific objectives, including sampling of different phases and determining phase ratios, for example. This will be discussed later as an example in the Claims under the Protocol Claims. In summary, capsules may now be classified and referred to as either A.sub.i,j or B.sub.i,j, or AB.sub.i,j.

4. Capsule Incubator and Manipulator (Also Evolutionary Compatible with Capsule Designs)

The system integrally designed Capsule Incubator and Manipulator machine performs a series of functions, including preserving the integrity of the in-vivo obtained conditions until such time and under said conditions each and every obtained sample can be either: stored, transported or tested and analyzed. The Manipulator positions the Capsule, constrains it, removes the collected samples cartridge and then can either insert it into a similar sealed capsule for archive storage or for transport, or insert it into a second platform testing cartridge, where the sample spools are removed and placed into the traverse testing table with its own indexing and motor drive identical dimensionally and characteristically or otherwise compatible mating parts to the sample collection cartridge drive and indexing mechanisms. This sample spools transfer is all done robotically, or technician remote assisted, under an equivalent "bell jar" in-vivo simulated and controlled environment, whereupon both the samples and technicians are protected in conformance with biological specimen handling protocols. The samples once placed in the portable traversing-indexing and forward/reverse spooling cartridge are now ready for temporary storage in an in-vivo simulated environment, or for immediate testing and characterization.

5. Analyzer

A comprehensive system of probes and instrumentation systems are both specifically designed, and in some cases selected off the shelf, to measure the chemical composition and characteristics of substances. The probes and data acquisition system are also integrally designed to be compatible dimensionally, electronically, and logistically with the samples collection and temporary storage system. In particular, special chemicals will be searched for as toxins to the human immune system, and the environment in which they were generated will be known, and through reverse energetics calculations, how they were created can be determined. Likewise, the same exact sample can be non-destructively examined microscopically to identify and characterize microbes existing at each instant and position and associated with the chemical compositions at the same exact position in the intestinal tract. Thus, the all-important role of microbes, especially bacteria and fungi, can be ascertained. All data are recorded on computer-based data acquisition systems in data bases and spreadsheet formats suitable for comprehensive statistical, graphical and other analysis methods, much of which will be automatically performed, included modeling in simulated real time, and 3-D computer graphics models of the processes taking place within and along entire length L of the intestinal tract.

6. Computer-Based Data Acquisition, Reduction, Analysis, and Display System (CBDARADS)

This system performs a variety of functions. All data from a wide variety of instruments in diverse formats must first be converted into a single compatible format for acceptance and manipulation by the system, so that it can then be processed. After appropriate electronic signal conditioning and standardized formatting, the output data from various instruments are converted first into SI units so that all future calculations will be simplified. Data are compiled into data bases and spreadsheets for viewing and designing further graphical displays and animations, which are then incorporated into the auto-processing/display mode to constitute in some applications, real-time data diagnostic and interpretation, and other uses. Since the data variables are expected to exhibit many interdependencies, a wide variety of animation variables will be selected.

7. Applications of the Invented System to Patients

Patient Preparation and Testing Protocols

Protocols are designed by a multidisciplinary team of physicians, and research scientists and engineers for designing the entire patient preparation and testing process beginning with: a) patient physician recommendations to accommodate the peculiarities and specific conditions of the patient to be tested and evaluated based upon symptoms as diagnosed by all attending physician(s), using other existing conventional medical diagnostic methods and equipment as guidance; b) patient physician and researchers specification of diet or other preconditioning; c) specific samples, sizes, quantity, to be collected to focus upon specific hypotheses, diseases, or other agenda; d) testing and diagnoses methodologies for the samples to focus upon specific hypotheses, diseases, or agenda; e) specific data presentation in specific computer graphic and other formats; and f) creation of individual patient intestinal flora profiles with intent to conduct further research to link said profiles or specific strains of bacteria, or combinations thereof, to patient existing diseases, or apriori prediction of risk for onset of specific future diseases that can also be accomplished by history matching of databases and previous profiles acquired by this same unique healthcare system.

8. Applications to Advancing Knowledge and Understanding of Human Gut

Many disciplines and branches of science and engineering have a vested interest in the processes taking place in the human gut, and as a result, the information that can be generated by this invented system. It is therefore anticipated that many research projects from a multitude of disciplines beyond the immediate medical sciences will be initiated, once this capability is available to the broad research community.

Although these data will be made available to multi-discipline specialists throughout the medical profession, it is anticipated that groups of diverse multi-discipline scientists and engineers will develop many special tests, procedures and protocols, employ and develop advanced research and clinical methodologies by applying multidisciplinary engineering principles, all to render the total process most effective and applicable to the most serious diseases and illnesses threatening human health that may have an origin in the human gut.

Applications to Advancing Knowledge, Science and Technology in Various Fields

The wealth of data and information collected from this human gut research and diagnostic system (RDS) can actually be used in many macro and micro branches of science, engineering and technology. As generally regarded as the most perfect machine, the human body processes often have applications that can be simulated and applied in other man made machines and technologies. One interesting aspect that can be investigated by the herein invented RDS is the energetics of the rapid and large volumes of intestinal tract gas production as a result of a patient ingesting wheat products, and having some "gluten sensitivity". Are these same "unknown, un-identified, and un-characterized" bacteria strains and colonies that are so capable of converting so efficiently gluten or other proteins, sulfur, or other biomaterials into gaseous products also useful in an external, commercial digester? These bacteria and their byproducts with the other substances need to be captured and held in captivity suitable for extensive research. This is only one of many readily identifiable possibilities for uses of said samples, data and information generated from the RDS. The spin off technologies of developing additional micro-miniature sensors and transducers should also be useful in many other applications.

10. Research and Medical Profession Protocols

A sample of substances or microbes, or set of elaborate data is only as good as the peripheral information of pre-existing conditions under which the information were obtained. Therefore, meaningful application of this RDS, of necessity, incorporates instruction sets under which it should be used, and some prior knowledge of the subject to which it is applied. Otherwise, interpretation of the data is not realistically possible. Also, before prescribing any medication or whatever following the obtaining of samples and data from the RDS, medical professionals must know the initial conditions anyway, and furthermore as a means of later evaluating effects after follow up uses of the RDS. Although such protocols would be necessary for patient applications, they are just as important in any research project as a matter of competent research methodology. As a result, and to also discourage and help avoid misapplication of the RDS, such protocols are considered part and parcel to the subject invention. This is also in part what led to the necessity of the unique RDS feature and method of simultaneously capturing all substances and the associated microbes at the same exact location and instant in time. There are also external, extraneous variables considered important to control as part of said protocols.

11. Analysis and Interpretation of Data

Although presentation of the data includes every conceivable manner of illustration to reveal all possible features as clearly and efficiently as possible, interpretation is the most important phase. In fact, interpretation may continue by case studies long after initial data sets are thoroughly displayed and analyzed for immediate decision making. Interpretation must also be done by a multi-disciplinary team, and standard formats will be introduced and developed as numerous data sets have been thoroughly analyzed by such teams.

Important Clarification Points for RDS

The present invention is a comprehensive method and process, complete with application protocols, and a unique apparatus and comprehensive, integrally-designed Research and Diagnostic System (RDS) with integrally designed components, for simultaneously obtaining samples of partially through completely digested food products or matter and the associated microbes, at the same exact location and time, along the entire human or other animal intestinal tract originating in the mouth and terminating at the end of the colon or anus. The present invention is able to be used is for obtaining samples of partially digested food products or digestive tract matter, as well as, microbes along the entire human, or other animal, gastrointestinal tract originating in the mouth and terminating at the end of the colon or anus. It should be noted that the present invention is able to specifically target either type of sample exclusively.

The present invention additionally provides a unique apparatus with integrally designed components for use with a comprehensive method and process, complete with application protocols integrally-designed Research and Diagnostic System (RDS). The system of apparatuses of the present invention comprises an electrical mechanical device, a capsule incubator and manipulator, an analyzer, and a computer-based data acquisition, reduction, analysis, and display system (CBDARADS).

The electromechanical device of the present invention, hereinafter referred to as a capsule, is designed, fabricated, and administered for ingestion by human research subjects or patients, in order to collect, store, and preserve, collected sample integrity and in-vivo environmental conditions from beginning to end of the intestinal tract, and beyond for chemical and biological testing when placed in a simulation incubator. The capsule comprises a specially designed housing, a thin film belt, and an electro-mechanical belt drive mechanism.

In current embodiment of the present invention, the capsule comprises a specially designed housing. The specially designed housing comprises special curvatures of defined algebraic functions, a porous permeable grid, and guidance rails. The special curvatures of defined algebraic functions serve a variety of purposes including ease of passage through intestinal tract, relative velocity of passage to that of food products, and position relative to intestine walls. The porous, permeable grid that readily allows processed food products and microbes to migrate through, yet safely separates it from the sidewalls of intestines. The guidance rails are for precisely locating and positioning of said capsule with sample collection belt with respect to the grid covered open window slot that receives sample products. Additionally, the specially designed housing is opaque to all wavelengths of radiation comparable to the human body shield that would be harmful to microbes or biochemical reaction or degradation processes. Furthermore, the specially designed housing is inert to contents of the gastro juices or intestinal tract contents and human immune system. Moreover, the specially designed housing provides ease of assembly, sealing, and recovery of sample collection cartridge.

In the current embodiment of the present invention, the thin film belt comprises imprinted/indented pockets. The imprinted/indented pockets comprise special patterns and special designed pocket and a thin film hermetic seal. The special patterns and special designed pocket s shapes, sizes and distributions as function of length, for sample collection to constitute a continuous sampling process at each point along the entire length L of the intestinal tract. The thing hermetic seal is applied to permanently cover the collection sample belt and its pockets to prevent sample contamination from one position to any other along the entire length L. The imprinted/indented pockets are positioned along the thin film belt, wherein the imprinted/indented pockets at the beginning and end of the thin film belt seal slit in the capsule housing to preserve initial sterile or post collection conditions of collected samples until such time the cartridge is removed from said housing. The imprinted/indented pockets being utilized for collected sample storage constituting an indexed collection method collecting up to 15,000 samples from beginning to end of intestinal tract.

In the current embodiment of the present invention the electro-mechanical belt drive mechanism comprises a power source, a drive train, and an associated removable cartridge assembly. The thin film belt being easily removed, either robotically or via technician manual remote assist, under preserved environmental conditions and conveyed into another storage capsule housing, or transferred to an indexing table for samples testing, or any other testing apparatus. Additionally, the electro-mechanical belt drive mechanism has programmable revolutions per minute to accommodate belt traveling speed and thus sampling rate or frequency as a function of x, and a triggered power shut off switch to disengage and stop the belt when the end of the sampling belt is reached. Furthermore, the electro-mechanical belt drive mechanism being contained in a removable cartridge may be of any other design that accesses intestine contents, samples them, and appropriately stores them all of which is accomplished by a similar cartridge subsystem herein exemplified, since subject sample products vary from a slurry, such as the fluidic chyme in the duodenum, to solidified stools in the lower colon, so must the capabilities of the capsules.

In the current embodiment of the present invention, a version of the capsule, hereinafter referred to as capsule B.sub.i,j unless otherwise specified, is an all-in-one tool, with immediate monitoring and administration functions allowing the deliverability and release of medication or other substances to a specific location or at a specific time, or both independently, and interactively based upon measured values either from the intestinal substances, or conditions, or active or feedback responses measured from various human body organs or systems.

In current embodiment of the present invention, a version of the capsule, hereinafter referred to as capsule AB.sub.i,j unless otherwise specified, is capable of collecting some gaseous, liquid, or solid samples for later analysis, while simultaneously making some in vivo measurements resulting in combined and new capabilities of simultaneous quantitative measurements and samples collection utilizing Capsule based technology.

In the current embodiment of the present invention, the capsule incubator and manipulator provides for and facilitates the handling and maintenance of in vivo conditions, and retrieval of said taken samples while maintaining in vivo conditions, and placing said collected samples into another cartridge for storage or transport, or retrieving said samples from said cartridge and placing them with their container belt or tubular belt onto another indexing type of platform suitable for transport to and manipulation for use by an assortment of instrumentation and testing probes and a large variety of other laboratory instruments.

In the current embodiment of the present invention the analyzer comprises an assortment of instrumentation and testing probes and a large variety of other laboratory instruments and testing equipment including spectrometers, chromatographs, microscopes and SEMs, and numerous other equipment for determining mechanical, chemical, physical, biological, bio-energetic, electrical, fluid, thermal, and other properties of intestinal substances, and comprehensive microbiological testing, evaluation, classification, and characterization of known and unknown microbe strains and species according to Phylogeny Tree of living organisms, as well as an indexing table that provides each sample access to the numerous probes, which consist of newly designed and developed probes and interface devices and modified instruments suitable for interfacing with the intestinal sample indent storage pockets within the sample belts or the tubular vessels.

In the current embodiment of the present invention, the CBDARADS comprises a unique construction, assembly and combination of instrumentation, computer-based hardware and software systems, with unique data processing and display features, and capabilities of feedback when queried, or used in interactive patient applications developed for special requirements of RDS.

The present invention is a comprehensive method and process, complete with application protocols for a human intestinal tract Research and Diagnostic System (RDS) capable of generating sufficient data and information for constructing ultimately a comprehensive engineering simulation model of the human gut, comprised of sub-system models, including data suitable for determining coefficients of a variety of equations used to describe and simulate the flow, chemical, endothermic/exothermic, biochemical, aerobic/anaerobic, bioenergetics, microbiological, and many other aspects and characteristics of a functioning human gut. The method of the present invention is provided with sub-function models, master combined, and comprehensive models intended to elevate multiple macro and micro functions of the human gut, and their interactions, to various levels of abstraction for computer software simulation purposes, and ultimately to be used in conjunction with real, specific-patient data, for the evaluation of disease cause and effect relationships, and predicted, projected and simulated apriori impact evaluations of various medications and diets, including creation and development of new medications and diets, as a means of expediting improvement of human health, and disease prevention. The comprehensive method and process of the present invention uses the RDS to create a human gut flora profile, wherein said profile may lead to explanation of existing diseases, or apriori of future onset of specific diseases. The present invention is able to correlate specific flora strains or combinations thereof, as may be related to certain locations, with existing or future onset of specific diseases. The present invention is able to deliver custom medications/antibiotics by way of the RDS to certain location with existing or future onset of specific diseases, for inoculation and prevention. Furthermore, in the present invention, the RDS is applied to other animals, and used to learn of their gut system processes and functions, as well as, diagnostic purposes for their diseases and health problems, while allowing the subject system to be further tested and developed and applied safely in other animals while being perfected and extensively development for human applications. Moreover, the RDS can be appropriately adapted with lower cost for use as an extremely valuable multi-disciplinary teaching tool in medical and other schools as dietary and food research, and, of course, many other diseases not typically associated with the intestinal tract.

Additionally the present invention is an experimental Celiac disease protocol for the application of a Research and Diagnostic System (RDS) for use with human subjects in order to establish accurate cause and effect relationships in diagnosis of celiac and related disease progression in phases over a period of time as well as rates of severity. The present invention provides a system to investigate, wherein said investigated system such as the human, urinary and intestinal tracts, auto-immune, cardiovascular and other systems. The present invention provides a controlled environment for investigated systems, wherein the initial and current conditions under which the RDS is administered are maintained to have the exact same daily diet, level of exercise and other factors as constants for at least three consecutive days in order to establish a steady state conditions. The present invention provides an RDS for an investigated system, wherein the RDS is administered in similar to currently available capsulated mendicants. The present invention initiates a first cycle of RDS administration to investigated system on fourth consecutive day while maintaining same exact diet and routines as prior several days, wherein a cycle of RDS administration commences upon ingestion of RDS by investigated system and concluded upon expulsion/recovery of RDS from investigated system. The present invention then initiates a second cycle of RDS administration to investigated system upon completion of first cycle of RDS administration while maintaining same exact diet and routines as prior several days. After which the present invention initiates a third cycle of RDS administration to investigated system upon completion of second cycle of RDS administration while maintaining same exact diet and routines as prior several days. At which point the present invention performs tests and analysis of data for intestinal flora profile consistencies and similarities in terms of strains/species and populations, as well as, chemical substances and concentrations profiles, and create a statistical original condition for the first cycle, the second cycle, and third cycle of RDS administration.

The present invention then alters the controlled environment by way of changing investigated systems diet to gluten free diet while maintaining same routines for a period of two weeks. Upon altering the controlled environment the present invention initiates a first cycle of gluten-free RDS administration to investigated system at beginning of third week while maintaining same exact Gluten-free diet and routines as prior several days. At which point the present invention initiates a second cycle of gluten-free RDS administration to investigated system upon completion of first cycle of gluten-free RDS administration while maintaining same exact Gluten-free diet and routines as prior several days. After which, the present invention initiate a second cycle of gluten-free RDS administration to investigated system upon completion of first cycle of gluten-free RDS administration while maintaining same exact Gluten-free diet and routines as prior several days. The present invention initiates a third cycle of gluten-free RDS administration to investigated system upon completion of second cycle of gluten-free RDS administration while maintaining same exact Gluten-free diet and routines as prior several days. With all three cycles administered to completion the present invention performs tests and analysis of data for intestinal flora profile consistencies and similarities in terms of strains/species and populations, as well as constructing delta gut flora profiles, and delta substances profiles, by statistically significantly differentiating between the profiles the first cycle, the second cycle, and third cycle of Gluten-free RDS administration.

The present invention initiates analysis of the collected data by observing the differential different strains/species and relative populations of bacteria as a function of x and the differential different chemical compounds and concentrations as a function of x. the present invention then commences interpreting data of the differential different strains/species collected for presence of the particular strains of bacteria or "gluten loving bacteria" as well as, their relative position as functions of in order to target for control or elimination. Furthermore the present invention simultaneously commences interpreting data of the differential different chemical substances collected for presence of chemical substances created by the combined biochemical reactions and the bacteria processed food substances, for chemical substances of concern. With data collection and analysis completed the present invention creates a 3-D graphical and animated illustrations of collected and interpreted data. The invention then stores the data in databases and spread sheets for facilitated access by multidisciplinary groups for research purposes and various uses by the actions performed through these steps, users are able to gain greater insight into the digestive tract functions, processes, and resulting conditions threatening human health can be concluded, modeled and applied.

In the current embodiment of the experimental Celiac disease protocol for the application of a Research and Diagnostic System (RDS) for use with human subjects, the aforementioned RDS tests, and protocols as illustrated, provide for, but not limited to, the detection of and determination of characteristics of specific bacteria responsible for gluten related illnesses and diseases. Additionally, the resulting problematic chemical substances are identified and characterized. Furthermore, the said RDS and above illustrated processes can be applied to other intestinal tract disorders, and diseases originating in the gut and lead to cures for many other diseases within other anatomical systems.

In an embodiment of the present invention the RDS has the ability to providing to deliver and release medication or other substances to a specific location or at a specific time, or both independently, and interactively based upon measured values either from the intestinal substances, or conditions, as well as active or feedback responses measured from various human body organs or systems. The present invention accomplishes this by administering RDS containing medication or other substances to investigated system. The present invention then delivers RDS to a specific location or at a specific time, or both independently, and interactively, wherein the specific point of interest is any point of interest within the investigated system. upon delivering the RDS to the specific the location or at a specific time, the present invention then releases the medication or other substances from RDS based upon a preprogrammed criteria such as measured values either from the intestinal substances, or conditions, as well as active or feedback responses measured from various human body organs or systems, wherein the specific measurements include presence of chemical substances or microbes, upstream or downstream, or the results of any effects they may have had that resulted in any specific condition with specified parameters within the investigated system. The present invention then measures immediate effects of the released medication or other substance from the RDS at the specific location or at the specific time on the chemical substances, microbes, any other hypothesized phenomena or variable of interest, as well as any specific human autoimmune responses as reflected by preprogrammed measurement criteria present within the investigated system.

In an embodiment of the present invention the ability of the RDS to repeat tests and evaluations within the intestinal tract immediately caused by some diet or medication administration, or any perceived changes within the body that would warrant taking another capsule. Thus, within the time it takes for a test sampling capsule to be evaluated after passing, and any medication is administered, another capsule can be taken and the immediate change in the unique individual flora and biochemical substances profiles can be determined. This provides evaluation of immediate, or later, effectiveness, or positive or negative impacts of any drug, as well as provides insightful data to facilitate the immediate improvement and development of drugs, all based upon factual data. Furthermore, the present invention is able to reduce cycle time for new drugs development, testing, approval, and patient applications, such that specific capabilities have many research, legal, educational, clinical, technology development, and other applications to advance patient remedies and medical science and technology. Moreover, this embodiment of the present invention can provide a new system that allows, facilitates, and provides for merging of micro and macro data, and sciences, engineering, and technologies integration and simultaneous development for the human gut. This can eliminate many current 20+ year longitudinal studies and expedite research results by orders of magnitude in time savings.

In summary, the RDS and all of the associated testing and protocols should confirm the old adage that, “A person's body is what they eat”, but with a corollary phrase at the end of the sentence: “and in conjunction with the individual's unique gut flora profile, revealing of the predictable diseases it will suffer”. This is why some physicians believe in occasional “cleansing” of the gut. The only problem is that the “cleansing” act is not defined or understood and the results are unknown, at both the micro and macro levels. This invention can solve most of this mystery and dilemma.

Although the invention has been explained in relation to its preferred embodiment, it is to be understood that many other possible modifications and variations can be made without departing from the spirit and scope of the invention as hereinafter claimed.

General Device Structure and Capabilities

The embodiments herein comprise a device for acquiring samples of matter along an intestinal track of a user, wherein the device is a capsule device configured to be swallowed and passed through the intestinal track. The device comprises a housing defining an opening adapted to allow the samples of matter to pass into the housing; a sample collector and preserver cartridge disposed within the housing and defining a plurality of indentations and chambers, each having a volume configured to collect the samples of matter; and a motor disposed within the housing and configured to drive the cartridge for collecting the samples of matter at a predetermined rate and position as the capsule passes through the intestinal track.

The device further comprising a receiver, wherein the receiver is configured to monitor the process of the capsule by active telemetry. The device may include a battery, wherein the battery is configured to power the motor such as a wafer battery. Other means of power may include a small voltaic cell that is sustained by the acidic fluids in the stomach or any other known type of battery or timer.

The housing of the device may be a material which is opaque to light waves for protection of collected samples of matter. The housing may further include multiple ends wherein each end is attached by a thread and sealed with an O-ring. The device may also comprise a mesh attached to the capsule housing configured to prevent the belt from touching the lining, epithelium, villi or obtrusive parts of the intestines.

The device may perform acquiring samples by including a spool having a hermetically sealing film; wherein the spool and film are configured encapsulate the matter samples by attaching the film to the belt after the belt has collected the matter samples.

The device can be monitored or tracked within the position of the environment by x-ray, magnetic resonance imaging (MRI), or active telemetry.

The device may comprise one or more belts and cartridges. These serve a plurality of purposes, including:

1) substances of a variety to serve different purposes, such as microbe baits,
2) multi-purpose measuring instrumentation,
3) multi-purpose control means and systems of actuators and telemetry antenna to serve a plurality of applications, including both internal Capsule and external telemetry monitoring and control, and
4) Incidental to any and all specific combinations of these first three purposes and capabilities, collect in vivo data of circumstantial evidence of direct response behavior that will lead to proof of hypotheses and causes of gut biochemical and microbial processes, that among other things, result in autoimmune system responses, illnesses and diseases, and then ultimately lead to cures for gut diseases.

The belt and cartridge design concept, provides the greatest versatility in conjunction with simplicity as a means of accomplishing many tasks associated with the broad test objectives, purposes, functions, and tasks necessary in such a biomedical environment, and such a complicated anatomical system as the subject being investigated and treated. The belts incorporate three basic covers as a means of protecting substances delivered to the gut and the integrity of samples recovered from the gut, and protection needed in some cases for the tools, either from the gut environment, or the gut from some of the tools themselves. Since the complexity of the gut anatomy and processes taking place therein introduces multiples of hundreds of combinations of variables, the belt was conceived as the only practical means of meeting the demand for a large number of samples on one pass through the gut. As such, belts can be configured for prescribed tests. The different purpose belts are configured on cards as cartridges ready to fulfill different test applications, and to be slid into the housings. Likewise, there is a diversity of chamber sizes, shapes, numbers, and orientations, in configurations and combinations in any given cartridge, to accommodate a battery, micro-motor, and provisions for each test. This concept addresses application to current issues and provides for immediate adaptation of new belts to meet new medical research needs. That is, this design utilizing the belt means, can efficiently respond immediately with minimum time, adaptation, and cost, to evolutionary research and treatments based upon future medical profession needs yet to be discovered, especially those as a direct result from usage of the device capabilities and the new research methodologies being introduced that broadens the horizon of gut medical science beyond the gut, to the entire human and its many anatomical components.

The device may further comprise one or more sensors, including biosensors and nano-bio-sensors, to be used for obtaining data. The measuring instrumentation may, for example, include measurements of macro body properties such as pH, temperature, noise, or other biochemical gut process variables including micro, molecular, cellular, and microbial shapes, sizes and motions, and means of communication, that can be measured, especially as consequences of introduced special foods or other substances. This may even include very importantly, the ability to recognize and distinguish between different molecules by any means of any individual molecular properties. Of particular example is recognition of toxins produced as part of bacterial assisted digestive processes. Recognition of said toxins may be by macro fluid variables, such as pH, noise, temperature, or by such micro properties as molecular shapes, movements, vibrations, communications, or other distinguishable features, etc. Such capabilities being considered are currently emerging micro technologies, involving bio-nanotechnology and nanotechnology sciences with such applications as graphene, one atom thick layers of carbon on substrates, that form the basis of micro-type sensors incorporated into microchips. The control means may include both feedback, and feed-forward processes in an engineering sense, and said processes may be both animate and inanimate, individually and in combination, in nature. The animate nature may include all microbes, from viruses down to single cell animals, up to larger microbes of bacteria or larger, even macro size. Initially, special emphasis is placed upon using the inexpensive, readily available lab-on-a-chip technology, including cell-on-a-chip and organ-on-a-chip methodologies. Cells-on-a-chip are of special relevance and importance because of probable reversibility application in the detection, isolation, and characterization of toxins to the autoimmune system. The inanimate nature includes chemicals, and bio-chemicals as may be produced within the gut by microbes, as well as, for example, microchip based control means, and hybrid animate-inanimate means.

The housing largely consists of a circular cylinder type shell or enclosure, and two domed end pieces inserted into the cylindrical shaped main housing body with fine female threads, and (this color means delete) grooves for accepting O-rings as seals effectuated by the threaded mating parts, and a guide track fastened to the inside walls to receive, position, constrain, and allow easy installation and alignment of belts without any special knowledge, skill, or tools. Different main housing bodies are designed with special purpose ports to accommodate and match up with specific design belt configurations as mating parts with suitable tolerances and allowances. Variations in the housing ports include: sizes, shapes, orientations, and positions within the housing body. These differences result from the mating part requirements of different cartridge belt configurations to accommodate specific tests. The port geometries are associated with the functions to be performed by each belt corresponding to specific experimental tests. In general, there are three basic port-belt associations involving: 1) sample extractions from the gut, 2) substance delivery to the gut, and 3) associated sensors, transducers, actuators, and transmitters.

Exemplary Embodiment

This invention represents a goal accomplished through three other component inventions referenced as Inventions 1, 2, 3 and Capsules A, B, C, respectively. That is, the ultimate process or system capabilities was achieved through the invention and initialized development of three capsule devices and methods as being the minimal number of tools and sub-processes required to accomplish the overall goals and capabilities needed to introduce a new in vivo gut technology. In other words, to get to the required point of adequate gut health care delivery, the Capsules A, B, and C apparatuses and associated in vivo methodologies were perceived to be, as in the calculus of variations, the brachistochrone path. Reference as provided above under the title of this invention is made back to the individual detailed descriptions of those three inventions, so that discussion of this Invention 4 can focus on the performance, capabilities, and utilization of the resulting 3-component system as a comprehensive in vivo System with 3 complementary components being used in 3 different stages, phases and roles. Absent any one of these three complementary inventions, the ultimate System capabilities and requirements would be destroyed.

To start with, as a system, Invention 4 accomplishes what many college or university deans or provosts, or research directors, find difficult to achieve. It demands and receives, of necessity, teamwork crosscutting many academic disciplines and branches of science and engineering. The multidisciplinary, macro and micro, dynamic, animate system of thousands of coupled, interdependent variables requires the utmost research methodology. The capabilities of this Invention 4, hereinafter called the In Vivo System, or just "System", now push the development of and demand for complementary emerging technologies and other hi-tech infrastructure. Especially the limiting micro technologies are now under another microscope. So, as a System, the overall impact spans even beyond delivering improved human gut health care, as will be discussed later in more detail. As a System, with gut exploratory, discovery, characterization, diagnostic, and treatment capabilities involving fluids, chemicals, and microbes, with synergistic benefits from each of the contributing complementary components A, B, and C and their respective methodologies, the gut and its manifestations within the body take on different meanings and new perspectives. It now becomes the ultimate challenge and object of research for graduate students, faculty, diverse groups of medical professionals, and private enterprise innovators and entrepreneurs. This System process and collective methodology enables another world to be explored and researched utilizing these new tools, or data generated from them, whether experimentally in humans or other animals, or virtually in an abstract manner. It should become the next research project for the international human microbiome initiative with expedited development of the System. It should broaden the scope of microbes in bioengineering processes, and accelerate biosensor, micro-sensor, lab-on-a-chip applications, and nano-biosensor development. Thus, the System is a significant catalyst that will create demand and applications for a broad spectrum of new technologies, new businesses and industries, and new healthcare academic curricula and programs. These are just a few examples of enabling roles the System introduces into our technological society, in addition to gut healthcare.

Capabilities of the System for improving human gut health care fall into many different categories, each with many applications. Some of the innumerable applications are abstracted or cited as examples, as follows:

1. Discovery, isolation and characterization of new aerobes and anaerobes living within the gut;
2. Association of chemical substances with species and strains of microbes;
3. Determination of microbe associated chemical substances that provoke autoimmune responses;
4. Determine variability of 1, 2, and 3, e.g. among patients of different characteristics; and
5. Determining Distribution Functions (DF) for hundreds of variables in patients of different characteristics, or health conditions. One such subset itself consisting of a long list of DF may include anaerobes of thousands of species/strains as functions of "x" or other variables, in essence creating thousands of detailed gut flora profiles over the entire GI tract. Another such subset may include the gut anoxic environment DF as functions of diet, medications, and the like.

Other such subset DF may include:

a) unique patient gut flora profiles based upon innumerable control variables,
b) normal chemical substance compositions DF as part of healthy or unhealthy patients or diets,
c) chemical substances compositions DF as isolated and contributed by any one of thousands of microbe species/strains and in conjunction with diets;

6. Using results in 5 above, raise the gut to an even higher level of abstraction involving a multitude of variables and conduct computer simulations for a variety of purposes.
7. Verification or rejection, with conclusive evidence, of hypotheses as to the roles bacteria play in the digestive process, or specific illnesses, such as Celiac, gluten sensitivities, or allergies.
8. Addition of new onboard chip-based technologies, especially lab-on-a-chip based technologies, as enabled by the basic Capsules design and capabilities, with intelligence based components, most assuredly will result in major gut disease breakthroughs during the first year of usage.

In other words, there is a virtually endless list of enabled studies and applications involving thousands of variables individually and in combinations for research, patient diagnosis, and patient treatment when pursued with said System. It is quite significant that this System will readily generate so-called Big Data, for the gut, wherein very little site specific in vivo data currently exists on the gut, especially for the most important inaccessible portions of the jejunum and upper colon.

Research on the major human diseases, such as top four in cost (Alzheimer's, heart, cancer, and diabetes), have for over a century, been focused on characterization of the symptoms and the compromised anatomy of the organs by all possible means of x-ray, autopsies, sections, and chemical analysis of the foreign substances deposited in the organs. Now, the symptoms and diseased tissues have been characterized to the utmost, along with total body behavior type symptoms/syndromes, and books have been written on all of these conditions. All of these 1,000's of studies have not led to the first clue as to the cause of the diseases in these and various other organs. Alzheimer's is an excellent example. Amyloid-beta plaques and probably 100 or more hypothesized causes, such as aluminum, have been extensively researched, yet, no clue as to the real causes. Researchers have been mesmerized by these symptoms in the diseased organs. This is believed by this inventor and researcher to be a huge oversight, with the actual causes having their origin in the gut. There are substantial reasons to hypothesize this for many diseased organs. Therefore, this invented technology is designed to thoroughly explore and research the gut for causes of the top ten or so diseases.

This inventor further hypothesizes that various strains of microbes and their byproducts create a host of conditions and substances that over extended time of months and years create the observed conditions and symptoms in the various organs. Specially designed capsules employed in this research offer a plethora of capabilities to explore, discover, capture, analyze, and characterize the gut matter of interest, which is many strains of bacteria, or other microbes, and the byproducts and changes they make to the normal gut environment, which introduces conditions or processes causing not only dysfunction of the gut from performing its normal roles, but also, introducing phenomena that show up as diseases in organs far removed from the gut. This is believed to be viable explanations for such devastating diseases as dementia, Alzheimer's, gluten sensitivities, Parkinson's, Autism, diabetes, cancer, and numerous others.

As a means of attempting to reduce the numbers of extraneous variables in this disease research, one of the objectives for one of the experiments is to attract special microbe strains expected to contribute the conditions leading to causes of specific diseases. In so doing, part of one experiment design is to use a small aperture to a very small chamber to allow a minute quantity of microbial and chemical substance matter to enter in a very short period of time and be captured and preserved. In addition, since special strains of bacteria are of interest, they are enticed by special attractions to enter the miniscule chambers. The enticements may be associated by various means or information with respect to a particular disease. One enticement, for example, could be considered as a special treat or bait for a special bacterium strain. Thus, a special device, and special methodology are required to accommodate these objectives and experiments. This is a first step in a methodical, logistical sequence of steps to follow the path to the causes of conditions showing up as "diseases" in various organs with a wide ranging variety of symptoms, both in the anatomy of the organ, and total body behavior of symptoms and syndromes, such as the aforementioned diseases.

This research is also pursuant to the initiatives of Congress in the National Alzheimer's Project Act for a Plan, which was released in May 2012, to prevent and effectively treat Alzheimer's disease by 2025. The United States and the world research communities must focus on causes of diseases, because the number of incidents and the costs are spiraling exponentially, and are already a threat to bankrupt some nations.

In summary, culmination of all contributions of Capsules A, B and C and all of the raw and calculated data created should result in sufficient information to allow, using Big Data in conjunction with other conventional scientific characterization and modeling methodologies, the creation of comprehensive, holistic models of the human gut system. This system should elevate the scientific level of knowledge of the gut as a system and its associated diseases by orders of magnitude. More importantly, this System should result in major breakthroughs of determining the causes and hopefully curing some of the major gut based diseases within the first year of application. Likewise, the enabling capabilities created by this System for family physicians, specialists, and the multitude of health care professionals, clinics, hospitals, and the pharmaceutical industries are enormous.

Finally, it is noteworthy to put into perspective the trillion or more microbes in the GI tract, probably exceeding 3,000 species/strains and all of the process variables they constitute, and then the combinatorial, factorial, combinations and permutations possibilities for isolating just basic cause and effect relationships. A methodology of statistically correlating extra body symptoms of illnesses and diseases or conducting narrow mono-disciplinary research as a means of isolating the causes of gut diseases would appear preposterous, and to date after 2,000 years, this has not been refuted. Then putting into perspective the herein invented in vivo technology, and how at least thousands of variables and millions of combinations are eliminated, so that tractable solution methodology can be used to isolate gut diseases should be of real significance, and a very high priority to develop within the United States of America. The Mayo Clinic estimates that over three billion dollars are spent on over-the-counter antacids, laxatives, acid blockers and fiber supplements alone for indigestion, not including prescriptions or serious diseases. The need for solutions to gut problems is among the world's greatest in healthcare, and this System is designed to have a major impact in a holistic manner.

Enhanced Embodiments

Approximately 33% of the U.S. population is estimated to now have some form of "gluten sensitivities". There is no single specific test, or combinations of tests, to absolutely conclude the existence of gluten sensitivities, or a related condition known as Celiac disease. A preponderance of blood sample tests for antibodies, are used to form a pattern of sufficient justification to conclude the condition may exist, which may typically include such symptoms in various degrees and combinations of: bloating, indigestion, acid reflux, diarrhea, constipation, inflammation in any one or more organs of the body, rashes, etc. Often, these symptoms are identified as separate diseases. Inflammatory arthritis, alopecia, various allergies, autism, dementia, Alzheimer's, IBS, Parkinson's, and numerous other neurological, cardiovascular, and other diseases in other systems fall into these categories. Autoimmune responses that create inflammation in numerous organs are examples of secondary effects that can result in various nutrient deficiencies, and many bioengineering processes that result in advanced stages, and are named various diseases in different organs.

In summary, the embodiments herein including methodologies and technologies, are of such nature to constitute an entirely new human healthcare system, and to revolutionize and create an entirely new hybrid, multidisciplinary, field of gastroenterology and give support to entirely new university graduate school multidisciplinary curricula syllabi, and new hybrid multidisciplinary university research programs, along with new government medical research programs and facilities. The number one human health disease killer is heart disease. The significance of these inventions is that the technology is directly applicable to the top four U.S. diseases in cost and incidents, which includes heart disease, Alzheimer's, cancer, and diabetes, all with a known origin in the gut.

The scope of these new specific claims comprise additional instruments and sub-devices, such as nanobots, housed within the capsule, and from which they can be launched and operate out of as a satellite base of operation. Such devices may be just extended from while attached to the capsule, or tethered from, or launched as autonomous micro or nanobots that can return upon command to the base capsule. Such satellite micro or nano-devices may also be attached by various means to the mucosal layer of the gut for predetermined extended periods of time to further either treat an area, or acquire data over some predetermined period of time, and by various predesigned measures detach itself from the gut interior surface and be expelled in the normal process of stool progression and expulsion.

Deployment of substances may include small objects of micro shape and size to perturb the autoimmune system, including all possible combinations, such as, "seeds" for prostate cancer treatment, which at the molecular and cellular levels may induce responses from the autoimmune system it may recognize as a threat.

Example

A device being designed is a micro syringe needle biopsy apparatus, wherein commands are sent to the capsule to move into position using various schemes of conveyor, belt, ramp, etc. to position a hollow needle of such dimension to extend beyond the housing of the capsule through an O-ring sealing type of arrangement, and step two by command to an actuator thrust, perhaps 1/16th of an inch into the adjacent gut wall for the purpose of obtaining a sample of the mucosal layer of gut tissue simultaneously along with a sample of gut adjacent substances that includes a micro sample size of microbes and their associated biochemical substances. Thus, specificity of microbes, tissue, and associated substances are of a 1,000th scale. Therefore, specificity and resolution are of the same micro order scale for all three of the tissue, microbes and their associated substance molecules. This is truly monumental in eliminating trillions of extraneous variables, if for no other reason, that it is estimated that there are typically 3,000 strains and species of microbes in the human gut, along with each of their multiplicity of byproduct substances. Simultaneous sampling and analysis of even just microbes and their substances has never been done in the gut.

Therefore the embodiment detailed is to simultaneously sample/analyze and associate damaged tissue, microbes, and chemical byproduct substances at the cellular and molecular micro scales is the ultimate theoretically possible capability for research and solution of the mysteries of disease causes throughout the entire history of the medical profession and medical science.

Such specificity and resolution at the micro scale is of paramount importance, and actually necessary, in order to determine the actual causative mechanisms and processes that constitute the origin of innumerable diseases. The contrast of this methodology against conventional statistical methodologies of correlating only symptoms resulting from many trillions of variables at huge macro scales over diverse locations and extremely different time intervals, and totally different transient gut environment conditions is literally astronomical.

Within the embodiment, the term "nanobot" is not limited only to the example above. Within the known technology, nanobot can additionally be understood to include such terms as: "nanorobotics", "nanite", "nanomachine", "a robot that allows precise interactions with nanoscale objects, or can manipulate with nanoscale resolution", "biochip of nanoelectronics", "MRI-guided nanocapsules", "nanomedibots", "molecular machine", "nanomedicine", "nanoparticles", "nanomaterials", "nanoshells", "microscopic robots" and any other relate technology or terms within nanotechnology.

The device of the embodiment is capable of enclosing substances and devices to be controlled by the device for the purposes of collecting, perturbing, deploying and releasing. The collecting step is to obtain samples from the surrounding environment including but not limiting to samples such as nodules, microbes, villi, tissue, mucosa, bacteria, fluids and the like. Further, the device can be controlled to obtain a sample from a first location and release the sample at a second location as a form of transposition.

The deployment step is to release substances or devices held within the capsule. As mentioned above, the deployment can be of samples obtained from the device. The substances and devices may also be stored within the device prior to swallowing the device. The substances and devices used may be one or more of the following: medicines, chemical substances, enzymes, antibiotics, proteins, microbes, fecal matter, fecal transplants, any type of microbes, dissolvable devices, needles, sample collecting units, nanobots or sensors. The substances and devices used for deployment can be tethered or untethered, autonomous, or allowed to just go with the flow, to the device when executing deployment, wherein the tethered substances and devices may be retracted back within the device capsule. Further, a step of injecting the surrounding environment may further be performed by use of the substances and devices which can be deployed.

Further, the device is capable of housing sensors for deployment or for sensing within the device itself. The type of sensors included may perform functions of sensing for body temperature, heart rate, breathing rate, pH levels, audio, electrocardiograms, pulse oximetry, fatigue, dehydration, tachycardia, shock, hypothermia, hyperthermia, fever, activity, GI pressure for manometry (barometer), neural dust, biosensors and the like. Additionally, the sensors could comprise an image sensor for obtaining image data of the surrounding environment.

The housing of the device may further be comprised of silicon, dissolving coatings, acrylic, elastics polymers, polymer gels, gelatin, Biolefin, paraffin wax, egg whites or any other known material or methods.

The actuation of controls, functions, or movements within the device may further include using ultrasound, magnetic fields, pH level activations, wireless actuation, real-time camera response, clock timing, x-ray imaging, and the like. The communication from an external device may further include use of any wireless communication such as radio, near-field, Bluetooth, Wi-Fi, and the like.

The device is configured to be the general size of a swallowed device. The embodiments of the present invention are built in varying lengths, but may be equal or less than 20 millimeters in width. Preferably, most of the devices are around 12 millimeters or less in width similar to swallowable capsules used today.

What is claimed:

1. A capsule device configured to be swallowed and passed through the intestinal track to be used for one or more purposes of collecting samples of matter within a environment within a gut, perturbing the environment within the gut, measuring the environment within the gut, sensing the environment within the gut and dispensing substances or additional smaller devices along the intestinal tract, the device comprising:

a housing defining an opening adapted to allow at least one of sample matter, substances or small devices to pass into and out of the housing, wherein the shape of the capsule device and housing are of a capsule type shape;

at least one of a motor and an actuator within the housing or an onboard autonomous and telemeter controlled circuitry; and at least one belt disposed within the housing and defining a plurality of indentations, each of the indentations having a volume configured to perform at least one of collecting and dispensing samples of matter, wherein the housing further comprises at least one of a substance or a small device, the at least one of the substance or the small device is deployed when the capsule device is actuated, wherein the substance or the small device is deployed during a process for collecting samples of matter within the environment within the gut.

2. The capsule device as claimed in claim 1, further comprising a receiver, wherein the receiver is configured to monitor the process of the capsule by active telemetry.

3. The capsule device as claimed in claim 1, wherein the deployed substance is at least one of medicines, specific chemicals, antibiotics, proteins, microbes, bacteria, fecal matter, fluids, and enzymes.

4. The capsule device as claimed in claim 1, wherein the deployed small device is a needle.

5. The capsule device as claimed in claim 1, wherein the small device can be tethered to the device.

6. The capsule device as claimed in claim 1, wherein the belt performs collecting a first sample at a first location of intestinal tract, wherein the first sample is combined with at least one of the substance or the small device within the housing to create a second sample; and the second sample is deployed at a second location of the intestinal tract, the second sample including at least one of the first sample and a deployed substance or small device.

7. The capsule device as claimed in claim 1, wherein the capsule device is further capable of collecting a plurality of samples at a plurality of locations along the intestinal tract when the capsule device is used in a single pass through the intestinal tract.

8. The capsule device as claimed in claim 1, wherein the capsule device is further capable of deploying a plurality of a substances or small devices at a plurality of locations along the intestinal tract when the capsule device is used in a single pass through the intestinal tract.

9. A method for diagnosing or treating disease associated with a gut or intestinal tract using a capsule device, comprising:

providing a capsule device configured to be swallowed and passed through the intestinal tract of a patient, wherein the capsule device comprises:

a housing defining an opening adapted to allow at least one of sample matter, substances or small devices to pass into and out of the housing, wherein the shape of the capsule device and housing are of a capsule type shape, at least one of a motor and an actuator within the housing or an onboard autonomous and telemeter controlled circuitry, and at least one belt disposed within the housing and defining a plurality of indentations, each of the indentations having a volume configured to perform at least one of collecting and dispensing samples of matter, wherein the housing further comprises at least one of a substance or a small device;

actuating the control of the capsule device so that the housing presents an opening;

deploying the at least one of the substance or the small device when the capsule device is actuated; and collecting samples of matter within the environment within the gut after the substance or the small device is deployed, wherein the samples of matter collected comprising at least one of the substance or the small device.

10. The method as claimed in claim 9, the capsule device further comprising a receiver, the method further comprising monitoring, by the receiver, the process of the capsule by active telemetry.

11. The method as claimed in claim 9, when deploying the substance, the substance is at least one of medicines, specific chemicals, antibiotics, proteins, microbes, bacteria, fecal matter, fluids, and enzymes.

12. The method as claimed in claim 9, when deploying the small device, the small device is a needle.

13. The method as claimed in claim 12, wherein the small device can be tethered to the device.

14. The method as claimed in claim 9, wherein the method further comprises:

collecting a first sample at a first location of intestinal tract; and deploying a second sample at a second location of the intestinal tract, wherein the second sample including at least one of the first sample and a deployed substance or small device.

15. The method as claimed in claim 9, wherein the method further comprises:

collecting a plurality of samples at a plurality of locations along the intestinal tract when the capsule device is used in a single pass through the intestinal tract.

16. The method as claimed in claim 9, wherein the method further comprises:

deploying a plurality of a substances or small devices at a plurality of locations along the intestinal tract when the capsule device is used in a single pass through the intestinal tract.

17. A method for collecting samples of the gut or intestinal tract using a capsule device, the method comprising:

providing a capsule device configured to be swallowed and passed through the intestinal tract of the patient, wherein the capsule device comprising:

a housing comprising an aperture used to collect a sample, wherein within the housing a specific chemical substance or a protein has been placed; and at least one a motor and an actuator within the housing; and actuating the capsule device at a specific time, wherein the actuating causes the aperture to be opened for a period of time, wherein during the period of time that the aperture is opened, samples of the gut or intestinal tract are capable of entering a chamber area of the capsule device where the specific chemical substance or the protein has been placed, wherein, once the period of time has elapsed, the aperture is closed and sealed preserving the samples of the gut or intestinal tract entered, the preserved samples are held within the capsule device during passage through the intestinal tract.

18. The method as claimed in claim 17, further comprising:

wherein at a second specific time, actuating the capsule device so to deploy a substance used to lubricate or expedite passage of the capsule device through the intestinal tract.

19. The method as claimed in claim 17, further comprising:

wherein the aperture is closed and sealed before further interference by normal gut downstream processes where water is extracted.

20. The method as claimed in claim 17, further comprising:

wherein, once the aperture is closed and sealed, the state of the capsule device and the samples are one of monitored, sensed or measured from within the capsule device, wherein real-time data can be communicated via telemetry of the capsule device.

* * * * *